(12) United States Patent
Py

(10) Patent No.: US 7,779,609 B2
(45) Date of Patent: *Aug. 24, 2010

(54) METHOD OF FILLING A DEVICE

(75) Inventor: Daniel Py, Stamford, CT (US)

(73) Assignee: Medical Instill Technologies, Inc., New Milford, CT (US)

( * ) Notice: Subject to any disclaimer, the term of this patent is extended or adjusted under 35 U.S.C. 154(b) by 572 days.

This patent is subject to a terminal disclaimer.

(21) Appl. No.: 11/714,004

(22) Filed: Mar. 5, 2007

(65) Prior Publication Data

US 2007/0156102 A1 Jul. 5, 2007

Related U.S. Application Data

(63) Continuation of application No. 10/265,075, filed on Oct. 3, 2002, now Pat. No. 7,186,241.

(60) Provisional application No. 60/327,128, filed on Oct. 3, 2001.

(51) Int. Cl.
*B65B 55/04* (2006.01)
*B65B 3/04* (2006.01)

(52) U.S. Cl. ............... 53/426; 53/467; 53/477; 53/167; 53/284.5; 53/285; 141/2; 141/18; 141/85; 141/329

(58) Field of Classification Search ............ 53/425, 53/426, 432, 467, 477, 167, 284.5, 285, 510; 141/2, 18, 82, 85, 329
See application file for complete search history.

(56) References Cited

U.S. PATENT DOCUMENTS 2,503,147 A 4/1950 Applezweig ............... 226/116

(Continued)

FOREIGN PATENT DOCUMENTS

| CA | 1123792 | 5/1982 | ........... 210/49 |
|----|---------|--------|--------|
| CA | 2396558 | 8/2001 | |

(Continued)

OTHER PUBLICATIONS

Supplementary European Search Report completed Sep. 21, 2009 in European Application No. 04 70 6030.

(Continued)

*Primary Examiner*—Stephen F Gerrity
(74) *Attorney, Agent, or Firm*—McCarter & English, LLP

(57) ABSTRACT

A syringe and a reconstitution syringe are provided for the delivery of controlled doses of any of numerous different sterile substances, such as vaccines, medicaments, pharmaceutical preparations, cosmetics, and food products. A plunger of the syringe defines a resealable stopper frictionally and slidably received within a hollow syringe body for dispensing the medicament or other substance through a dispensing tip of the syringe upon movement of the plunger. The resealable stopper defines a heat-sealable portion to allow the stopper to be penetrated by a needle or other filling device to fill the syringe with a medicament or other substance, and in turn allow the hole remaining upon withdrawal of the needle to be heat sealed by transmission of laser energy thereon. The plunger assembly further defines a plurality of cam-like members that each engage and cooperate with a respective helical path of steps formed on the inner wall of the syringe body to provide stepwise movement of the plunger and, in turn, precise metering of the substance dispensed therefrom. A reconstitution syringe defines within a syringe body plural compartments, wherein each compartment stores a respective component of a multi-component medicament or other preparation. An elastomeric plug is coupled to the plunger and connected between the two compartments to prevent intermixing of the components. Upon moving the plunger, the plug is released to thereby place the compartments in fluid communication with each other, and to facilitate intermixing of the components upon shaking the syringe.

22 Claims, 10 Drawing Sheets

U.S. PATENT DOCUMENTS

| | | | |
|---|---|---|---|
| 2,648,334 A | 8/1953 | Brown et al. | 128/218 |
| 2,667,986 A | 2/1954 | Perelson | 215/48 |
| 2,797,837 A | 7/1957 | Buford | |
| 3,092,278 A | 6/1963 | Järnhäll | 215/37 |
| 3,101,863 A * | 8/1963 | Jackson, Sr. | 215/247 |
| 3,136,440 A | 6/1964 | Krug et al. | 215/47 |
| 3,193,128 A | 7/1965 | Ravn | 215/42 |
| 3,278,063 A | 10/1966 | Kranzhoff | 215/38 |
| 3,340,671 A | 9/1967 | Loo | 53/37 |
| 3,353,718 A | 11/1967 | McLay | 222/158 |
| 3,358,865 A | 12/1967 | Andersen | 215/38 |
| 3,392,859 A | 7/1968 | Fischer | 215/39 |
| 3,424,329 A | 1/1969 | Hershberg et al. | 215/37 |
| 3,537,498 A | 11/1970 | Amand | |
| 3,637,102 A | 1/1972 | Shaw | 215/40 |
| 3,659,749 A | 5/1972 | Schwartz | 222/145 |
| 3,662,753 A | 5/1972 | Tassell | 128/218 M |
| 3,685,248 A | 8/1972 | Godelaine | 53/37 |
| 3,699,961 A | 10/1972 | Szpur | 128/218 M |
| 3,811,591 A | 5/1974 | Novitch | 215/12 R |
| 3,838,689 A | 10/1974 | Cohen | 128/218 M |
| 4,041,994 A | 8/1977 | Horwitz | |
| 4,048,255 A | 9/1977 | Hillier et al. | 260/859 R |
| 4,050,459 A | 9/1977 | Sanchez | 128/218 C |
| 4,185,628 A | 1/1980 | Kopfer | 128/218 M |
| 4,189,065 A | 2/1980 | Herold | 222/46 |
| 4,205,754 A | 6/1980 | Nielsen et al. | 215/249 |
| 4,250,611 A | 2/1981 | Wong | 29/460 |
| 4,251,003 A | 2/1981 | Bodenmann | |
| 4,265,364 A | 5/1981 | Baba | 215/249 |
| 4,346,708 A | 8/1982 | LeVeen et al. | 128/236 |
| 4,366,912 A | 1/1983 | Matukura et al. | 215/247 |
| 4,367,739 A | 1/1983 | LeVeen et al. | 128/236 |
| 4,390,111 A | 6/1983 | Robbins et al. | 220/259 |
| 4,419,323 A | 12/1983 | Winchell | |
| 4,444,330 A | 4/1984 | Kasai et al. | 215/247 |
| 4,456,138 A | 6/1984 | Bereziat | 215/232 |
| 4,471,879 A | 9/1984 | Connor et al. | 215/249 |
| 4,475,905 A | 10/1984 | Himmelstrup | 604/208 |
| 4,479,578 A | 10/1984 | Brignola et al. | 206/221 |
| 4,499,148 A | 2/1985 | Goodale et al. | 428/447 |
| 4,635,807 A | 1/1987 | Knapp | 215/247 |
| 4,643,723 A | 2/1987 | Smit | 604/207 |
| 4,664,275 A | 5/1987 | Kasai et al. | 215/247 |
| 4,664,277 A | 5/1987 | Connor | 215/249 |
| 4,682,703 A | 7/1987 | Kasai et al. | |
| 4,703,781 A | 11/1987 | Meyer et al. | 141/5 |
| 4,815,619 A | 3/1989 | Turner et al. | 215/248 |
| 4,834,152 A | 5/1989 | Howson et al. | 141/286 |
| 4,838,877 A | 6/1989 | Massau | |
| 4,842,028 A | 6/1989 | Kaufman et al. | 141/114 |
| 4,910,435 A | 3/1990 | Wakalopulos | |
| 4,962,868 A | 10/1990 | Borchard | 222/49 |
| 4,968,625 A | 11/1990 | Smith et al. | |
| 4,973,318 A | 11/1990 | Holm et al. | 604/208 |
| 5,009,654 A | 4/1991 | Minshall et al. | |
| 5,031,675 A | 7/1991 | Lindgren | 141/291 |
| 5,038,839 A | 8/1991 | Morimoto et al. | |
| 5,060,659 A | 10/1991 | Cook et al. | |
| 5,085,332 A | 2/1992 | Gettig et al. | 215/249 |
| 5,088,612 A | 2/1992 | Storar et al. | 215/247 |
| 5,088,995 A | 2/1992 | Packard et al. | 604/415 |
| 5,088,996 A * | 2/1992 | Kopfer et al. | 141/329 |
| 5,101,991 A | 4/1992 | Morifuji et al. | |
| 5,129,212 A | 7/1992 | Duffey et al. | 53/426 |
| 5,215,538 A | 6/1993 | Larkin | 604/249 |
| 5,226,462 A | 7/1993 | Carl | |
| 5,226,895 A | 7/1993 | Harris | 604/208 |
| 5,247,015 A | 9/1993 | Bayan | 525/99 |
| 5,290,260 A | 3/1994 | Stines | 604/224 |
| 5,341,854 A | 8/1994 | Zezulka et al. | 141/1 |
| 5,344,036 A | 9/1994 | Stanescu et al. | 215/251 |
| 5,360,413 A | 11/1994 | Leason et al. | 604/249 |
| 5,364,369 A | 11/1994 | Reynolds | 604/187 |
| 5,379,908 A | 1/1995 | Rohe | 215/249 |
| 5,390,469 A | 2/1995 | Shimizu et al. | |
| 5,411,065 A | 5/1995 | Meador et al. | 141/1 |
| 5,414,267 A | 5/1995 | Wakalopulos | |
| 5,423,791 A | 6/1995 | Bartlett | 604/403 |
| 5,425,465 A | 6/1995 | Healy | 215/355 |
| 5,435,076 A * | 7/1995 | Hjertman et al. | 53/510 |
| 5,464,111 A | 11/1995 | Vacek et al. | 215/249 |
| 5,484,566 A | 1/1996 | Gabbard | 264/250 |
| 5,496,302 A | 3/1996 | Minshall et al. | |
| RE35,203 E | 4/1996 | Wakalopulos | |
| 5,514,339 A | 5/1996 | Leopardi et al. | 422/99 |
| 5,545,147 A | 8/1996 | Harris | 604/209 |
| 5,549,141 A | 8/1996 | Meador et al. | 141/1 |
| 5,573,516 A | 11/1996 | Tyner | 604/249 |
| 5,591,136 A | 1/1997 | Gabriel | 604/211 |
| 5,612,588 A | 3/1997 | Wakalopulos | |
| 5,620,434 A | 4/1997 | Brony | 604/406 |
| 5,630,800 A | 5/1997 | Blank et al. | 604/82 |
| 5,641,004 A | 6/1997 | Py | 141/3 |
| 5,673,535 A | 10/1997 | Jagger | |
| 5,702,019 A | 12/1997 | Grimard | 215/301 |
| 5,718,348 A | 2/1998 | Manera | |
| 5,728,075 A | 3/1998 | Levander | 604/211 |
| 5,743,889 A | 4/1998 | Sams | 604/211 |
| 5,744,087 A | 4/1998 | Williams et al. | 264/297.2 |
| 5,749,201 A | 5/1998 | Cochrane | |
| 5,779,668 A | 7/1998 | Grabenkort | 604/89 |
| 5,785,683 A | 7/1998 | Szapiro et al. | 604/89 |
| 5,816,772 A | 10/1998 | Py | 414/786 |
| 5,823,373 A | 10/1998 | Sudo et al. | 215/249 |
| 5,842,321 A | 12/1998 | Jones | |
| 5,871,110 A | 2/1999 | Grimard et al. | 215/249 |
| 5,876,372 A | 3/1999 | Grabenkort et al. | 604/89 |
| 5,879,336 A | 3/1999 | Brinon | 604/191 |
| 5,902,298 A | 5/1999 | Niedospial, Jr. et al. | |
| 5,909,032 A | 6/1999 | Wakalopulos | |
| 5,931,828 A | 8/1999 | Durkee | 604/403 |
| 5,957,898 A | 9/1999 | Jepson et al. | 604/256 |
| 5,971,181 A | 10/1999 | Niedospial, Jr. et al. | 215/247 |
| 6,004,298 A | 12/1999 | Levander | 604/211 |
| 6,006,932 A | 12/1999 | Morini | 215/249 |
| 6,021,824 A | 2/2000 | Larsen et al. | 141/329 |
| 6,050,435 A | 4/2000 | Bush et al. | 215/250 |
| 6,068,150 A | 5/2000 | Mitchell et al. | 215/247 |
| 6,070,748 A | 6/2000 | Storar | 215/249 |
| 6,083,201 A | 7/2000 | Skinkle | 604/151 |
| 6,095,355 A | 8/2000 | Jessen et al. | 215/247 |
| 6,126,640 A | 10/2000 | Tucker et al. | 604/187 |
| 6,140,657 A | 10/2000 | Wakalopulos et al. | |
| 6,145,688 A | 11/2000 | Smith | 220/259 |
| 6,168,037 B1 | 1/2001 | Grimard | 215/301 |
| 6,199,350 B1 | 3/2001 | Brechel et al. | |
| 6,223,918 B1 | 5/2001 | Browne | 215/249 |
| 6,234,335 B1 | 5/2001 | Gee et al. | 215/247 |
| 6,267,154 B1 | 7/2001 | Felicelli et al. | 141/18 |
| 6,269,976 B1 | 8/2001 | DeJonge | |
| 6,308,494 B1 | 10/2001 | Yuyama et al. | |
| RE37,471 E | 12/2001 | Jagger | |
| 6,343,711 B1 | 2/2002 | Coughlin | |
| 6,360,794 B1 * | 3/2002 | Turner | 141/329 |
| 6,364,864 B1 | 4/2002 | Mohiuddin et al. | |
| 6,382,441 B1 | 5/2002 | Carano | 215/247 |
| 6,385,943 B2 | 5/2002 | Yuyama et al. | |
| 6,481,571 B1 | 11/2002 | Kelders et al. | |
| 6,499,615 B1 | 12/2002 | Szieff et al. | |
| 6,544,257 B2 | 4/2003 | Nagase et al. | |
| 6,568,439 B1 | 5/2003 | Se et al. | |
| 6,604,561 B2 | 8/2003 | Py | |
| 6,684,916 B2 | 2/2004 | Py | |

| | | |
|---|---|---|
| 6,805,170 B2 * | 10/2004 | Py .................... 141/2 |
| 6,971,551 B2 | 12/2005 | Widgery |
| 7,000,806 B2 * | 2/2006 | Py et al. .......... 222/386.5 |
| 7,018,389 B2 | 3/2006 | Camerlengo |
| 7,032,631 B2 | 4/2006 | Py |
| 7,100,646 B2 | 9/2006 | Py et al. |
| 7,243,689 B2 * | 7/2007 | Py .................... 141/2 |
| 7,290,573 B2 * | 11/2007 | Py et al. ............ 141/329 |
| 7,500,498 B2 * | 3/2009 | Py .................... 141/329 |
| 2001/0009990 A1 | 7/2001 | Hostettler et al. ...... 604/209 |
| 2001/0041872 A1 | 11/2001 | Paul, Jr. ............ 604/167.04 |
| 2002/0006353 A1 | 1/2002 | Bilstad et al. |
| 2002/0010995 A1 | 1/2002 | Thibault et al. ........... 29/511 |
| 2002/0018731 A1 | 2/2002 | Bilstad et al. |
| 2002/0023409 A1 | 2/2002 | Py |
| 2002/0029022 A1 | 3/2002 | Naritomi et al. ......... 604/256 |
| 2002/0131902 A1 | 9/2002 | Levy ...................... 422/99 |
| 2002/0161334 A1 | 10/2002 | Castellano et al. ....... 604/187 |
| 2002/0172615 A1 | 11/2002 | Woodworth et al. |
| 2002/0193752 A1 | 12/2002 | Lynn ..................... 604/249 |
| 2003/0098286 A1 | 5/2003 | Bloom et al. |
| 2003/0156973 A1 | 8/2003 | Bilstad et al. |
| 2006/0137998 A1 | 6/2006 | Spector et al. |
| 2009/0229702 A1 * | 9/2009 | Py ..................... 141/2 |

FOREIGN PATENT DOCUMENTS

| | | |
|---|---|---|
| DE | 86 13 068 U1 | 6/1986 |
| DE | 295 15 681 U1 | 12/1995 |
| EP | 0 480 196 | 4/1992 |
| EP | 0 511 183 A1 | 10/1992 |
| EP | 0 921 151 | 10/2001 |
| EP | 0 921 151 B1 | 10/2001 |
| FR | 2509689 | 7/1981 |
| GB | 500354 | 2/1939 |
| GB | 984149 | 2/1965 |
| GB | 2091229 | 7/1982 |
| GB | 2364700 | 2/2002 |
| GB | 2364700 A | 2/2002 |
| WO | WO 95/34381 | 12/1995 |
| WO | WO 2005/018707 | 9/2003 |
| WO | WO 2004/026695 | 4/2004 |
| WO | WO 2007/120719 | 10/2007 |

OTHER PUBLICATIONS

Supplementary European Search Report completed Dec. 17, 2009 in European Application No. 03 79 7876.

* cited by examiner

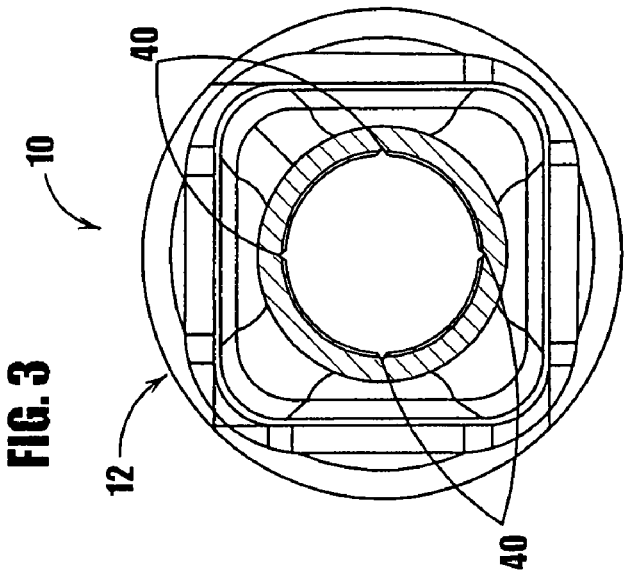
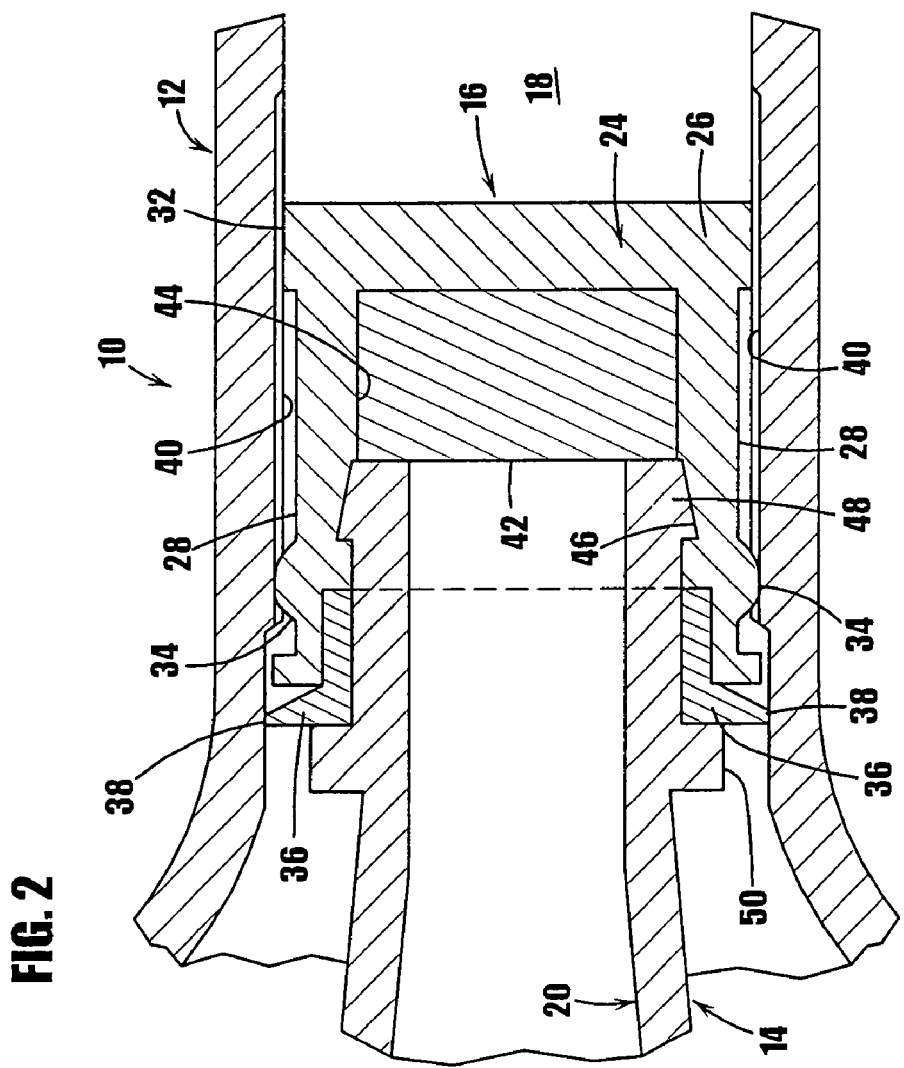

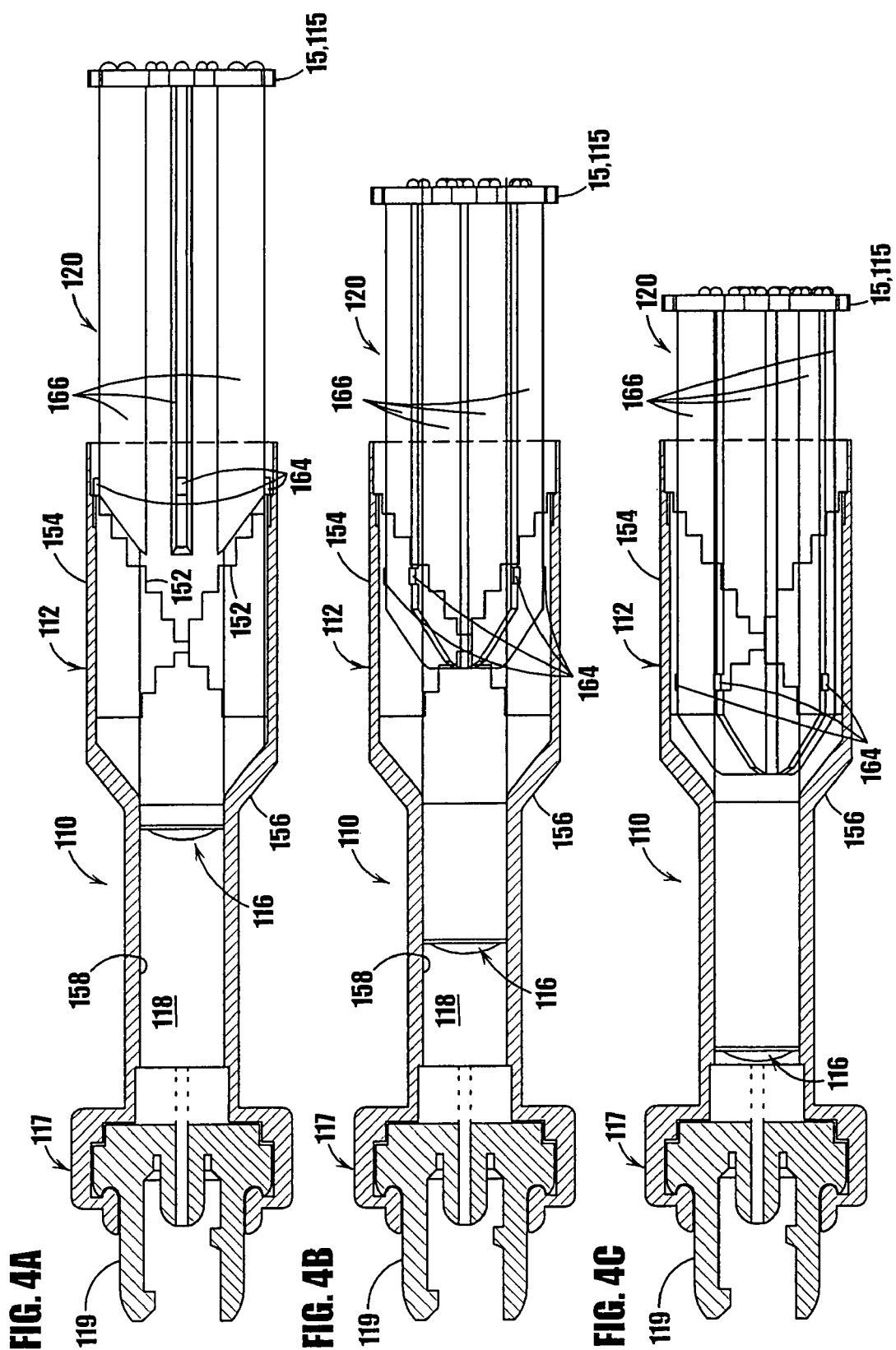

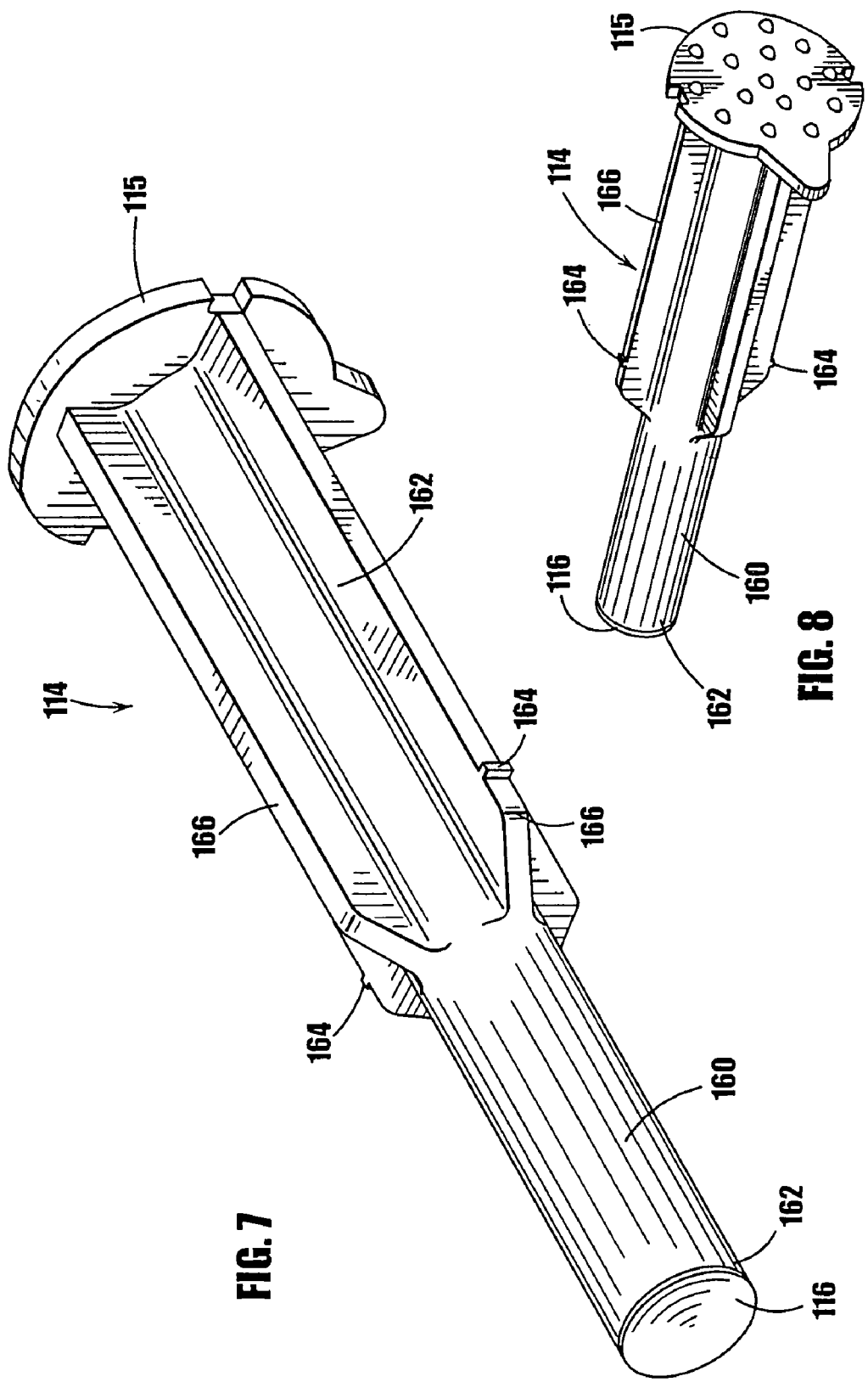

METHOD OF FILLING A DEVICE

CROSS-REFERENCE TO RELATED APPLICATION

This patent application is a continuation of U.S. application Ser. No. 10/265,075, filed Oct. 3, 2002, entitled "Syringe And Reconstitution Syringe", now U.S. Pat. No. 7,186,241, issued Mar. 6, 2007, which claims the benefit of U.S. Provisional Application Ser. No. 60/327,128, filed Oct. 3, 2001, entitled "Syringe And Reconstitution Syringe", the contents of which are hereby expressly incorporated by reference as part of the present disclosure.

BACKGROUND

The present invention relates to syringes for delivering controlled, metered doses of any of numerous different substances to humans or animals, such as vaccines, medicaments and pharmaceutical preparations. The syringes of the present invention may include means for controlling the travel of the plungers in the syringes for delivering precise amounts of the substances contained within the syringes. The syringes of the present invention also may include fusible or heat sealable stoppers connected to, or otherwise forming the plungers, for hermetically sealing the interfaces between the plungers and the interiors of the syringes, and thereby preventing ingress of air or contaminants through the plungers and into contact with the medicaments or other substances contained within the syringes.

A typical prior art syringe includes a hollow syringe body, a plunger slidably received within one end of the hollow body, and a needle connected to the other end of the hollow body. The plunger is moved through the syringe body to, in turn, eject through the needle the medicament or other substance contained within the syringe. The syringe body typically defines a transparent, graduated cylinder, and the user visually aligns the plunger tip with the appropriate graduation to dispense a desired amount of medicament or other substance from the syringe. One of the drawbacks associated with this type of syringe is that physicians, practitioners and other users may become tired, have difficulty focusing on the graduations, and/or may shake or otherwise have difficulty precisely aligning the plunger with the correct graduation(s) on the syringe body. As a result, human error or physical impairment can easily cause a user to dispense the incorrect amount of medicament or other substance from the syringe, and similarly prevent a user from precisely metering a constant dosage from one application to the next. When dispensing medicaments, accurate and controlled delivery is critical, particularly for avoiding overmedication. Overmedication can especially occur when the medicament is in the form of a liquid or other type of fluid.

Several devices described in the prior art permit controlled doses of medicaments to be delivered. These devices can be complicated to manufacture, assemble and fill with medicaments. As a result, these devices can be expensive to manufacture and may not be useful for vaccines, over the counter ("OTC") medicaments, and other types of pharmaceutical preparations. Another disadvantage of these prior art devices is that air can enter the device during filling and/or storage after the device is filled. Air entering the device during filling or storage can cause degradation of the medicament or other substance contained therein, reducing the efficacy of the medicament or other substance, and/or causing spoilage which may require that the medicament or other substance be discarded.

For some medicaments, preservatives are added to prevent degradation or spoilage of the medicament before use due to ingress of air or other contaminants. The preservatives can react with the medicament, however, reducing its efficacy. Also, some users can have undesirable adverse reactions to the preservatives in the medicaments.

Accordingly, it is an object of a currently preferred embodiment the present invention to provide a syringe that can be filled with a sterile substance, such as a vaccine, medicament or other pharmaceutical preparation, while maintaining the sterility of the syringe and substance during filling and storage thereafter. It is yet another object of a currently preferred embodiment of the present invention to provide a syringe with a heat sealable and/or fusible stopper on the plunger that prevents ingress of air or other contaminants through the plunger and into the substance contained within the syringe.

It is also an object of a currently preferred embodiment of the present invention to provide a syringe including means for providing a metered dose of a substance contained within the syringe, such as a vaccine, medicament or pharmaceutical preparation. It is another object of a currently preferred embodiment of the present invention to provide a syringe that can be relatively inexpensive to manufacture, easy-to-use and that provides a metered dose of a vaccine or other medicament, pharmaceutical preparation or other substance.

It is an object of another currently preferred embodiment of the present invention to provide a reconstitution syringe including multiple chambers for storing multi-component substances, such as vaccines, and other medicaments and pharmaceutical preparations, whereby the components can be mixed immediately prior to use and metered doses of such substances can be dispensed from the syringe.

SUMMARY OF THE INVENTION

One aspect of the present invention is directed to a syringe that may be used for the delivery of any of numerous different sterile substances, such as vaccines, medicaments, pharmaceutical preparations, cosmetics, and food products. In accordance with one aspect of the present invention, the syringe comprises a syringe body defining therein a chamber for receiving a predetermined substance to be dispensed from the syringe. A plunger of the syringe is slidably received within the syringe body for dispensing the substance upon movement therein. The plunger includes a resealable stopper penetrable by a needle or like filling member for introducing the predetermined substance through the stopper and into the chamber of the syringe body. The penetrable region of the resealable stopper is fusible in response to the application of thermal energy thereto for hermetically sealing the penetrable region upon removing the needle or like filling member therefrom.

In one embodiment of the present invention, the resealable stopper includes a base portion formed of a first material compatible with the predetermined substance contained within the syringe. The base portion defines a peripheral surface for slidably contacting an inner wall of the syringe body and a substance-exposed surface defining the portion of the stopper exposed to the predetermined substance contained within the syringe. A resealable portion overlies the base portion, and both the resealable portion and base portion are penetrable by the needle or like filling member for introducing the predetermined substance through the stopper and into the syringe body. The penetrable region of the base portion is substantially infusible in response to the application of thermal energy thereto, and the penetrable region of the resealable portion is fusible in response to the application of thermal energy thereto for hermetically sealing the penetrable region upon removing the needle or like filling member therefrom.

In another embodiment of the present invention, the penetrable region of the resealable stopper is heat resealable to hermetically seal the needle aperture by applying laser radiation at a predetermined wavelength and power thereto. The resealable stopper comprises a thermoplastic body defining (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal a needle aperture formed in the needle penetration region thereof in a predetermined time period of less than approximately 2 seconds and substantially without burning the needle penetration region. In a currently preferred embodiment of the present invention, the needle penetration region is formed of a thermoplastic blend of a first material consisting essentially of a styrene block copolymer and a second material consisting essentially of an olefin. Preferably, the first and second materials are blended within a range of about 50:50 to about 95:5 by weight.

In one embodiment of the present invention, the syringe includes means for controlling the travel of the plunger assembly to deliver a pre-determined dose of the substance contained within the syringe. The means for controlling the travel of the plunger assembly may include, for example, cam-like members formed on the upper guide portion of the plunger assembly which engage and cooperate with steps formed on the inner wall of the upper chamber of the syringe body. As the plunger assembly is rotated, the cam-like members travel along the steps to create step-wise movement of the plunger assembly into the syringe. The step-wise movement results in delivery of a precise, pre-determined quantity of the substance contained in the syringe with each step-wise or incremental movement of the plunger.

Another aspect of the present invention is directed to a syringe provided in the form of a reconstitution syringe that includes multiple compartments for storage of any of numerous different multi-component substances for forming vaccines, medicaments, or other pharmaceutical preparations. In a currently preferred embodiment of the present invention, the syringe body includes an upper chamber, a transition portion, and a lower chamber that contains the compartments for storage of the multi-component substances. The plunger assembly preferably includes an outer frame which extends to a point within the lower chamber of the syringe body. At the end of the outer frame within the lower chamber of the syringe body, an elastomeric plug is held in an opening in the outer frame. A closure member is contained within the outer frame of the plunger assembly and extends from the top of the syringe body to approximately the top of the lower chamber of the syringe body. The closure member includes a base that seals the lower portion of the outer frame. In a currently preferred embodiment of the reconstitution syringe of the present invention, the top of the closure member includes a plurality of cam-like members which engage steps on the inner wall of the syringe body, or like means for providing step-wise movement of the plunger assembly.

Also in a currently preferred embodiment of the present invention, the reconstitution syringe includes two compartments for storing the multiple components of the substance to be contained within the syringe body. The first compartment is defined by the walls of the outer frame, the base of the closure member, and the inner surface of the end of the outer frame, including the elastomeric plug. The second compartment is formed in the lower portion of the syringe body and is defined by the dispensing tip and the outer surface of the end of the outer frame, including the elastomeric plug.

In use, the first compartment of the syringe contains a first component of a multi-component vaccine, medicament or other preparation, which is typically a fluid, such as a saline solution or a solvent. The second compartment contains a second component of the preparation, which may be a powder, a liquid, or another fluid or lyophilized product. To mix the two components, the closure member is held in place and the outer frame is withdrawn from the syringe body until a snap engagement on the upper portion of the closure is engaged by the outer frame. As the outer frame is withdrawn, the fluid in the first compartment exerts pressure on the elastomeric plug, causing the plug to be released and thereby placing the first and second compartments in fluid communication with each other and allowing the first and second components to intermix. The elastomeric plug acts as a mixing ball to thereby provide means for facilitating mixing of the two components and, in turn, provide a multi-component mixture. The outer frame and closure cooperate to form the plunger mechanism for delivery of the preparation.

To create a hermetically-sealed compartment for storage of the preparation in the syringe, the currently preferred embodiments of the present invention include a fusible or heat sealable stopper at the base of the plunger. The compartment(s) for storage of the preparation is (are) filled by inserting a needle, such as a non-coring, double lumen needle, through the fusible stopper into the storage compartment. As the storage compartment is filled, the air in the storage compartment is allowed to escape through an annular one-way valve formed on the outer periphery of the fusible stopper. After the storage compartment is filled, the heat sealable insert on the fusible stopper is heated, such as by laser transmission, to fuse the hole created by the needle, and the one-way valve on the outer periphery of the fusible stopper returns to its normal position to hermetically seal the interface between the plunger and the interior of the syringe.

One advantage of the currently preferred embodiments of the present invention is that the fusible or heat sealable stopper on the plunger provides a hermetically sealable interface between the plunger and the interior of the syringe, thus preventing contamination of the interior of the syringe during filling and storage of the syringe. In addition, the resealable stoppers enable the syringes of the present invention to be filled with a sterile substance, such as a vaccine, medicament or other pharmaceutical preparation, while maintaining the sterility of the syringe and substance during filling and storage thereafter. In addition, the currently preferred embodiments of the present invention may be relatively inexpensively manufactured, thereby allowing the syringes to be used with a wide variety of substances, including liquids, cremes and ointments.

Another advantage of the currently preferred embodiments of the present invention is that they provide means for delivering controlled doses of vaccines, medicaments and other pharmaceutical preparations.

Yet another advantage of the currently preferred embodiments of the reconstitution syringe of the present invention is that the separable components of the vaccine, medicament or other preparation can be stored separately until immediately prior to use, which is especially advantageous for multi-component substances that have a relatively short shelf life when mixed.

Other advantages of the syringes of the present invention will become more readily apparent in view of the following detailed description of the preferred embodiments, claims and accompanying drawings.

BRIEF DESCRIPTION OF THE DRAWINGS

FIG. 2 is a partial, cross-sectional view of the fusible or heat sealable stopper of the syringe of FIG. 1.

FIG. 3 is a cross-sectional view of the heat sealable stopper and syringe body of FIG. 2.

FIGS. 4A through 4C are somewhat schematic, partial cross-sectional views of a second syringe embodying the present invention including means for effecting step-wise movement of the plunger within the syringe body, and illustrating the progressive movement of the plunger within the syringe body.

FIG. 7 is a perspective view of the plunger of the syringe of FIG. 4.

FIG. 8 is another perspective view of the plunger of the syringe of FIG. 4.

DETAILED DESCRIPTION OF THE INVENTION

Figure 1:
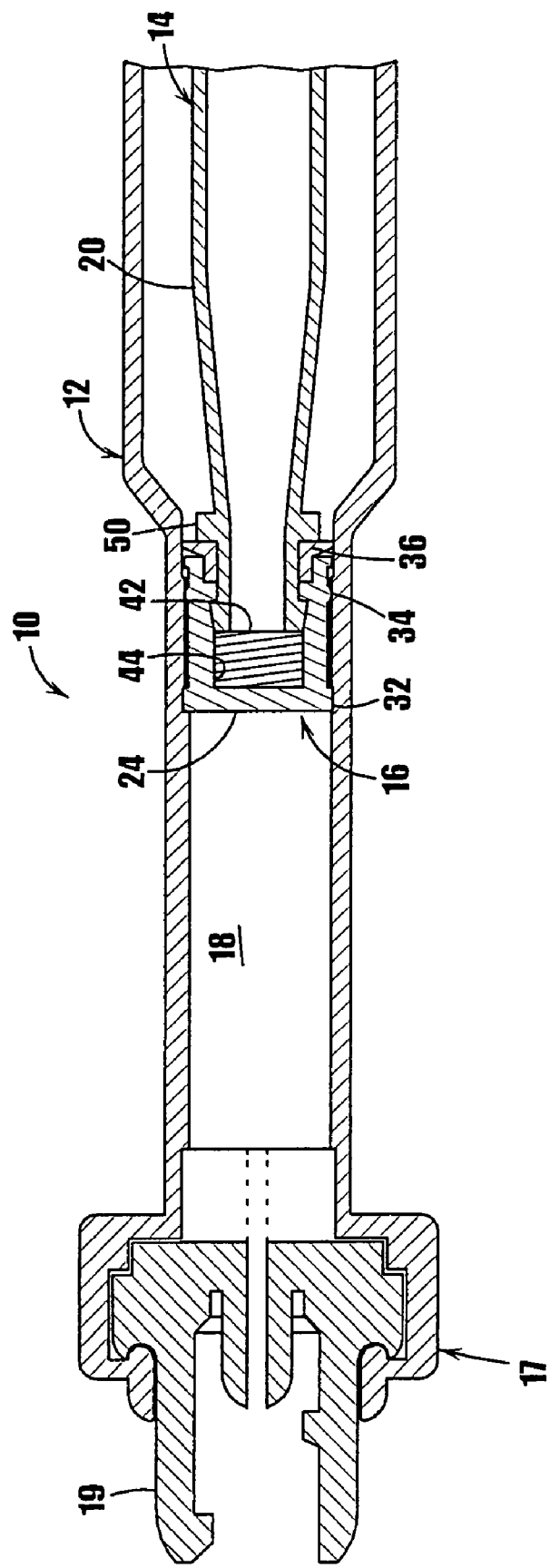
FIG. 1 is a partial, cross-sectional view of a syringe embodying the present invention.

As shown in FIGS. 1 and 2, the present invention relates to an improved syringe 10 for delivery of controlled doses of sterile substances, such as vaccines, medicaments and other pharmaceutical preparations. The syringe 10 comprises a syringe body 12 and a plunger assembly 14. A fusible or heat sealable stopper 16 is provided at the base of the plunger 14 to hermetically seal a chamber 18 of the syringe and thereby prevent ingress of air or contaminants into contact with the sterile substance contained therein. As described further below, the currently preferred embodiments of the present invention preferably include means for controlling the travel of the plunger in the syringe which results in the delivery of a relatively precise amount of the sterile substance in the syringe. In addition, as shown in FIGS. 9-13, the syringe of the present invention may take the form of a reconstitution syringe including multiple compartments to allow separate storage of the components of a multi-component substance, such as a vaccine, medicament or pharmaceutical preparation, prior to use. This can be especially advantageous where the medicament has a relatively short shelf life.

As used herein, the term "syringe" means a device used to inject or deliver a substance such as a liquid, creme, ointment or other fluid into a body or onto the skin. In addition, the term "plunger" is used herein to mean a device used to exert pressure on a substance such as a liquid, creme, ointment or other fluid contained within a chamber of a syringe.

Hermetically Sealed Syringe Assembly

In a preferred embodiment of the present invention illustrated in FIGS. 1-3, the syringe 10 comprises a syringe body 12 and a plunger assembly 14. In accordance with the present invention, the plunger assembly 14 includes a heat sealable or fusible stopper 16 allowing the syringe to be filled in a sterile filling machine of the type disclosed in commonly-assigned U.S. patent application Ser. No. 09/781,846, filed in the name of Dr. Daniel Py, which is hereby expressly incorporated by reference as part of the present disclosure. The syringe body 12 is generally cylindrical; however, as shown typically in FIG. 3, the outer surface of the syringe body 12 may define a rectangular or other non-cylindrical shape to facilitate gripping, mounting within another device, or otherwise as may be required. A flange 15 (FIG. 4) or other means for gripping the syringe may be provided at the top of the syringe opposite a dispensing end 17 of the syringe used for dispensing the medicament or other substance contained within the syringe.

At the dispensing end 17 of the syringe, means 19 are provided to connect a hypodermic needle to the syringe body (not shown) to dispense the contents of the syringe. The means 19 for connection of a needle to the syringe body may take the form of any of numerous different devices or methods that are currently, or later become known for performing this function. For example, a conventional connection means marketed under the trademark LUER-LOK may be included at the end of the syringe to allow connection of a hypodermic needle. Other needle connection means, such as threaded fittings, elastomeric plugs, or fitted end caps equally may be used to attach a needle to the end of the syringe. The lower end 17 of the syringe body may be shaped or threaded as required in a manner known to those of ordinary skill in the pertinent art to accommodate the selected needle connection means 19. A cap or other means for hermetically sealing the dispensing end of the syringe (not shown) may be secured to the dispensing end 17 of the syringe until the hypodermic needle is connected to the syringe to dispense the medicament or other substance therefrom.

As shown best in FIG. 2, the plunger assembly 14 comprises a drive portion 20 fixedly attached to the fusible stopper 16. The drive portion 20 of the plunger is preferably in the form of a rod or other appropriate shape, and generally defines an outer diameter less than the inner diameter of the syringe body 12. As shown in FIG. 4, at the end of the drive portion 20 opposite the fusible stopper 16, a flange, knob or other gripping portion 15 is preferably provided for allowing a user to grip and, in turn, force the plunger into the syringe to deliver the medicament or other substance therefrom.

The fusible stopper 16 is provided at the base of the plunger 14 to hermetically seal the lower chamber 18 of the syringe. As shown in FIG. 2, the fusible stopper 16 is formed at the end of the plunger 14 and includes a resilient base 24 made of vulcanized rubber or like material which is known to those of ordinary skill in the pertinent art, and acceptable for use in the manufacture of stoppers or like elements placed in contact with or otherwise exposed to the sterile substance to be contained within the syringe. The lower portion 26 of the base 24 of the fusible stopper 16 defines a peripheral sealing surface 32 that is shaped and dimensioned to slidably and frictionally engage the inner wall of the syringe body 12. The base 24 of the fusible stopper further defines a peripheral wall 28 extending upwardly from the lower portion 26 of the base 24. The peripheral wall 28 defines an outer diameter slightly less than that of the sealing surface 32 and the inner diameter of the syringe body 12 to reduce the friction between the fusible stopper and the syringe body upon movement of the plunger therein.

At the upper end of the peripheral wall 28, an annular raised portion or protuberance 34 dimensioned to be frictionally received within the chamber 18 of the syringe body 12 further seals the plunger assembly 14 and prevents air from contacting the medicament contained within the syringe. At the top of the peripheral wall 28, a one-way valve is formed by a wedge-shaped, flexible annular flap 36, which is shaped and dimensioned to be flexible and to contact the inside of the syringe body 12 to form the annular one-way valve. The tip 38 of the flexible flap 36 makes contact with the inside of the syringe body 12 when the plunger is in its fully-retracted position. As shown in FIG. 2, in the illustrated embodiment of the present invention, the inside diameter of the syringe body 12 in the area of the one-way valve 36 may be slightly larger than the inside diameter of the syringe at the base 24 of the fusible stopper 16 when the plunger is in the illustrated retracted position. As the plunger 14 is advanced into the syringe body 12, the inside diameter of the syringe body decreases slightly, causing the flexible flap 36 to make increased contact with the syringe body, thereby sealing the lower portion of the syringe from ingress of air.

As shown in FIGS. 2 and 3, the inner wall of the chamber 18 of the syringe body 12 is provided with a plurality of axially-elongated grooves 40 angularly spaced relative to each other about the axis of the syringe. The grooves 40 are formed in the inner wall of the chamber 18 and extend in the axial direction from below the base 24 of the fusible stopper 16 when in the fully-retracted position and upwardly beyond the annular protuberance 34. As described below, the grooves 40 allow air contained in the syringe to escape as the syringe is filled with a medicament or other substance.

A resealable member 42 is contained within an upper recess 44 of the base 24 defined by the peripheral wall 28. The resealable member 42 is received within a recess 44 formed in the peripheral wall 28 of the base 24, and is secured in place by the end of the drive portion 20 of the plunger. The interior surface of the peripheral wall 28 of the fusible stopper is shaped with an annular groove 46. An annular flange 48 is formed at the end of the drive portion 20 and is dimensioned and shaped complementary to the annular groove 46 on the interior surface of the peripheral wall 28. Accordingly, the annular flange 48 is pressed, snapped or otherwise received within the annular groove 46 to fixedly secure the resealable stopper 16 to the drive portion 20. A second flange 50 is axially spaced relative to the first flange 48 to capture and retain the base 24 and the resealable stopper on the drive portion. In the embodiment of the invention shown in FIGS. 1 and 2, the drive portion 20 is in the form of a hollow tube to allow insertion of a filling needle to fill the chamber 18, and allow re-sealing of the needle hole after filling, as described in the above-mentioned co-pending patent application.

The resealable member 42 is preferably made of a resilient polymeric material, such as a blend of the polymeric material sold by Shell Oil Co. under the registered trademark KRATON® and a low-density polyethylene, such as the polyethylene sold by Dow Chemical Co. under the trademarks ENGAGE™ or EXACT™. However, as may be recognized by those skilled in the pertinent art based on teachings herein, other appropriate materials that are currently or later become known for performing the function of the heat sealable stopper equally may be used. An important feature of the resealable member 42 is that it be resealable to form a gas tight seal after inserting a needle or like injection member through the resealable member. Preferably, the resealable member 42 can be sealed by heating the area punctured by the needle with laser or other radiation transmission as described, for example, in the above-mentioned co-pending patent application.

To fill the chamber 18 of the syringe with the desired medicament, a hypodermic needle, a non-coring, double lumen needle, or other type of injection member is inserted through the resealable member 42 and the resilient base 24 of the fusible stopper 16 in order to dispense the medicament or other sterile substance into the chamber 18 of the syringe. As the medicament is injected into the chamber of the syringe, the air within the chamber is displaced by the medicament and forced out. The air escapes through the plurality of grooves 40 formed in the inner wall of the syringe body 12. At the top of the peripheral wall 28, the force of the escaping air causes the flexible flap 36 of the one-way valve to move away from the inner wall of the syringe body, allowing the air to pass out of the syringe body. When the syringe has been filled with the medicament or other substance, the flexible flap 36 returns to its normal position in contact with the syringe body 12, thereby forming a hermetic seal to prevent air from entering the syringe and contacting the medicament or other substance therein. As the plunger is inserted into the chamber 18 of the syringe, the grooves 40 terminate, and the chamber is further sealed by the peripheral sealing surface 32 and the annular protuberance 34 on the resealable stopper 16.

After the syringe 10 is filled with the medicament or other substance, the resealable member 42 is heated to fuse the hole formed by the needle or other filling member. If necessary, a laser (not shown) may be used to sterilize the surface of the resealable member prior to needle filling. In addition, the same laser or a different laser may be used to seal the hole remaining after filling. Preferably, the syringe is filled in a sterile filling machine, and in accordance with a method of the types disclosed in the above-mentioned co-pending patent application. The laser allows sufficient energy to be directed to the resealable member in the fusible stopper while avoiding heating of the medicament or other substance in the syringe. Other methods of heating the resealable member known to those skilled in the art may be used depending on the heat sensitivity of the medicament contained in the syringe and/or other factors.

Because the syringe is hermetically sealed after it is filled with the medicament or other preparation, the syringe may be stored for extended periods of time without spoilage due to ingress of air and without the addition of preservatives to prevent such spoilage.

In the currently preferred embodiments of the present invention, at least a portion of the resealable stopper is formed of a thermoplastic material defining a needle penetration region that is pierceable with a needle to form a needle aperture therethrough, and is heat resealable to hermetically seal the needle aperture by applying laser radiation at a predetermined wavelength and power thereto. In an alternative embodiment of the present invention, the entire body of the stopper is formed of the thermoplastic material. In another embodiment of the invention as described above, an overlying portion of the stopper if formed of the fusible thermoplastic material, and an underlying portion of the stopper is formed of an infusible material, such as vulcanized rubber. Preferably, each thermoplastic portion or body defines (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal the needle aperture formed in the needle penetration region thereof in a predetermined time period and substantially without burning the needle penetration region (i.e., without creating an irreversible change in molecular structure or chemical properties of the material). In a currently preferred embodiment, the predetermined time period is approximately 2 seconds, is preferably less than or equal to about 1.5 seconds, and most preferably is less than or equal to about 1 second. Also in a currently preferred embodiment, the predetermined wavelength of the laser radiation is about 980 nm, and the predetermined power of each laser is preferably less than about 30 Watts, and most preferably less than or equal to about 10 Watts, or within the range of about 8 to about 10 Watts. Also in a currently preferred embodiment, the predetermined color of the material is gray, and the predetermined opacity is defined by a dark gray colorant added to the stopper material in an amount within the range of about 0.3% to about 0.6% by weight.

In addition, the thermoplastic material may be a blend of a first material that is preferably a styrene block copolymer, such as the materials sold under either the trademarks KRATON or DYNAFLEX, and a second material that is preferably an olefin, such as the materials sold under either the trademarks ENGAGE or EXACT. In a currently preferred embodiment of the invention, the first and second materials are blended within the range of about 50:50 by weight to about 95:5 by weight (i.e., first material:second material). In one exemplary embodiment of the present invention, the blend of first and second materials is about 50:50 by weight. The benefits of such blends over the first material by itself are improved water or vapor barrier properties, and thus improved product shelf life; improved heat sealability; a reduced coefficient of friction; improved moldability or mold flow rates; and a reduction in hystereses losses. As may be recognized by those skilled in the pertinent art, these numbers and materials are only exemplary, however, and may be changed if desired or otherwise required in a particular system.

Hermetically Sealed Syringe With Step-Wise Movement

In FIGS. 4-8, another syringe embodying the present invention is indicated generally by the reference numeral 110. The syringe 110 is substantially similar to the syringe 10 described above with reference to FIGS. 1-3, and therefore like reference numerals preceded by the numeral 1 are used to indicate like elements. The primary difference of the syringe 110 in comparison to the syringe 10 is that the syringe 110 includes means for controlling the travel of the plunger 114 and effecting step-wise movement of the plunger to, in turn, dispense predetermined doses of the medicament or other substance contained within the syringe.

Figure 5:
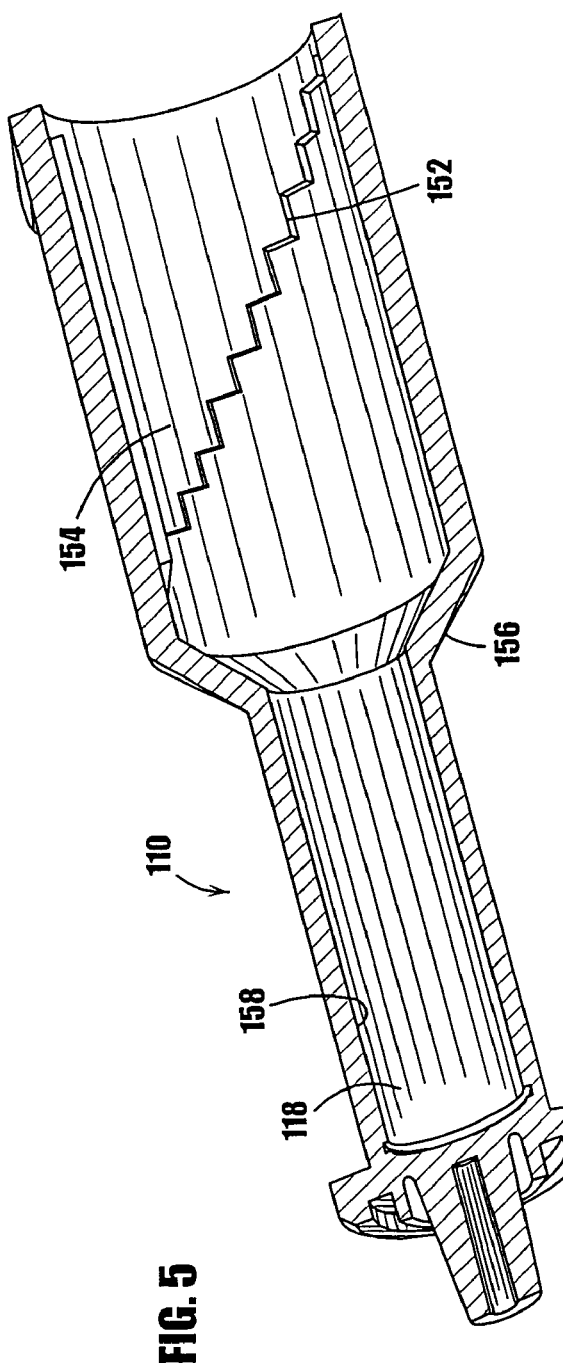
FIG. 5 is a perspective view of a first half of the syringe body of FIG. 4.
Figure 6:
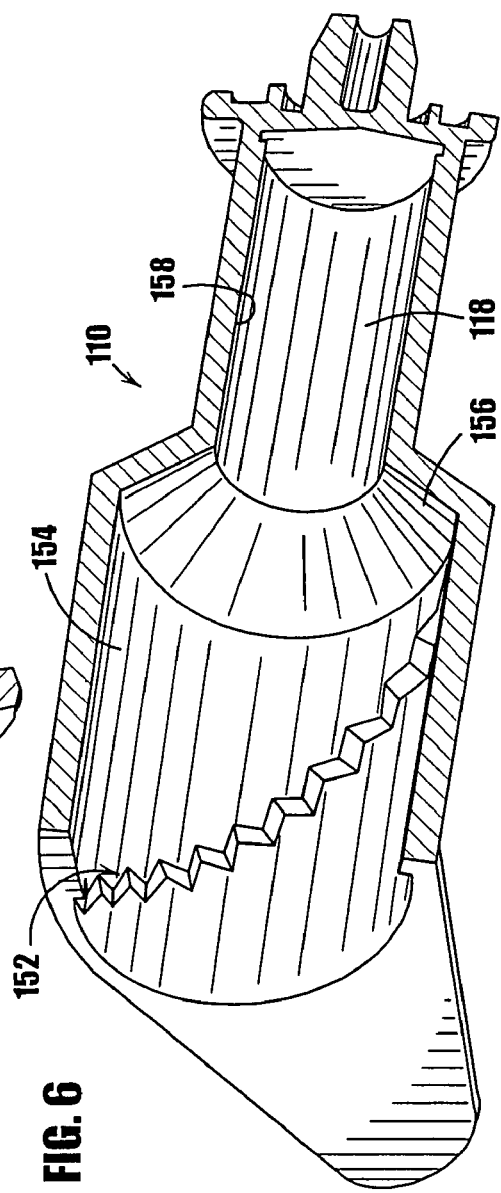
FIG. 6 is a perspective view of a second half of the syringe body of FIG. 4.

As shown in FIGS. 4-6, the inner walls of the syringe body 12 define a cylindrical cavity. The inner wall of the upper portion of the syringe body includes a plurality of steps 152 defining an approximately helical path. As shown in FIGS. 5 and 6, the inner wall of the upper portion of the syringe body 12 defines two helical sets of steps 152 formed on opposite sides of the inner wall of the upper chamber 154 of the syringe body relative to each other. Each set of steps 152 defines an approximately helical path. As shown in FIG. 5, one set of steps 152 is oriented to allow travel along the steps in the direction from the top of the upper chamber 154 toward a tapered portion 156 of the syringe body 112. As shown in FIG. 6, one set of steps 152 is oriented in the opposite direction relative to the other set of steps to prevent rearward movement of the plunger 114, as described further below.

As shown in FIGS. 4A-4C, the inner wall 158 of the lower chamber 118 of the syringe body 112 defines a smooth cylindrical cavity and has an approximately constant inner diameter over the axial length of the lower chamber. The lower chamber 118 of the syringe is used to contain the medicament or other substance, and is dimensioned to frictionally engage the resealable stopper 116 of the plunger 114 as described further below. The inner diameter of the lower chamber 118 is preferably constant to ensure that a specific quantity of the medicament or other substance contained therein is dispensed from the syringe for a pre-determined distance of travel by the plunger 114.

Referring now to FIGS. 7 and 8, the plunger 114 comprises of a lower drive portion 160 and an upper guide portion 162. A fusible stopper 116, as described in further detail above with reference to FIGS. 1 and 2, is fixedly attached to the end portion 162 of the plunger. The fusible stopper 116 contacts the medicament or other substance in the lower chamber 118 of the syringe during use. As described in detail above, the fusible stopper 116 is shaped and dimensioned to fit frictionally into the lower chamber 118 of the syringe body 112 to hermetically seal the lower chamber of the syringe. The drive portion 160 of the plunger 114 is shaped and dimensioned to fit within the lower chamber 118 of the syringe body. The outside diameter of the drive portion 160 is preferably at least slightly less than the inside diameter of the lower chamber 118 of the syringe body to reduce the frictional force generated by movement of the plunger within the syringe body. The lower drive portion 160 should be sufficiently long to be fully inserted into the lower chamber 118 of the syringe body.

The upper guide portion 162 of the plunger 114 defines two diametrically-opposed, cam-like members 164 that extend perpendicularly from the outside surface of the upper guide portion of the plunger. The cam-like members 164 cooperate with the steps 152 formed on the inner wall of the upper chamber 154 of the syringe body to provide means for controlling the travel of the plunger through the syringe in a stepwise manner. The cam-like members 164 are preferably located on the upper guide portion 162 such that the fusible stopper 116 is in contact with the medicament or other substance contained in the lower chamber 118 when the cam-like members 164 engage the top step 152 formed on the inner wall of the upper chamber 154 of the syringe body 112. The outside surface of the upper guide portion 162 of the plunger 114 preferably includes a plurality of vanes 166 or other support means to provide additional rigidity and/or strength to the plunger during use. A knob or other gripping portion 115 is formed at the upper end of the plunger 114 to provide means for the user to grip the plunger during use.

At the end of the lower chamber 118 of the syringe, means 119 are provided to connect a hypodermic needle to the syringe to dispense the contents of the syringe. The means 119 for connection of a hypodermic needle to the syringe body may be any one of several devices or methods that are currently, or later become known to those skilled in the art for performing this function. For example, a conventional connection means marketed under the trademark LUER-LOK may be included at the end of the syringe to allow connection of a hypodermic needle. Other needle connection means, such as threaded fittings, elastomeric plugs, or fitted end caps may be used to attach a needle to the end of the syringe instead. The lower end of the syringe body may be shaped or threaded as required to accommodate the selected needle connection means. A cap or other means for hermetically sealing the dispensing end of the syringe may be used until the hypodermic needle is connected to the syringe to dispense the medicament or other substance therefrom.

To deliver a dose of medicament or other substance contained within the syringe 110, the plunger 114 is rotated and depressed until the cam-like members 164 on the upper guide portion each travel down one step 152 along the inner wall of the upper chamber 154 of the syringe. The distance that the base 124 of the plunger travels is thereby precisely controlled, and a precise volume of the medicament or other substance can be delivered. The volume of substance delivered is a function of the height of the step 152 and the inside diameter of the lower chamber 118. By setting these two parameters, the volume of medicament delivered as a result of travel by the plunger along a single step may be precisely controlled. For example, if the inside diameter of the lower chamber of the syringe is 6 mm, and it is desired to have movement of the plunger assembly by one step result in the delivery of 100 microliters of the substance contained in the syringe, then the step height would be set at approximately 3.54 mm. Where the medicament includes an active ingredient and a carrier, the dose of active ingredient delivered also may be a function of the concentration of active ingredient in the carrier. Delivery of a higher dose can be achieved by instructing the user to move the plunger by the number of steps required to deliver the desired amount of the medicament. In the example provided above, movement by two steps would result in delivery of 200 microliters, etc.

As may be recognized by those skilled in the pertinent art based on the teachings herein, the structure for performing the function of controlling the travel of the plunger to effect step-wise movement of the plunger and dispense predetermined doses, can take any of numerous different configurations that are currently or later become known for performing this function. For example, this structure may take the form of any of the different thread configurations disclosed in commonly assigned U.S. patent application Ser. No. 60/403,484, filed Aug. 13, 2002 and entitled "Dispenser With Sealed Chamber And One-Way Valve For Providing Metered Amounts Of Substances", which is hereby expressly incorporated by reference as part of the present disclosure.

In one such exemplary embodiment, the means for controlling the travel of the plunger includes threads formed on the upper portion of the plunger assembly 14 that engage partial threads formed on the inner wall of the upper portion of the syringe body 12. The threads on the upper portion of the plunger define a plurality of regions in which the thread diameter gradually increases, beginning from a diameter that corresponds to the diameter of the partial threads on the inner wall of the upper portion of the syringe, to a diameter that is greater than the diameter of the partial threads. The largest diameter threads on the plunger have a smaller diameter than the diameter of the syringe body between the partial threads.

As the plunger is rotated, the larger diameter threads on the plunger are progressively engaged by the partial threads on the inner wall of the upper portion of the syringe body. This causes the upper portion of the syringe body to expand slightly. As the largest diameter threads on the plunger disengage from the partial threads on the syringe body and enter the area between the partial threads, the syringe body returns to its original diameter. When the larger diameter threads are located in the area between the partial threads, the plunger assembly is locked in position until sufficient force is applied to the plunger assembly to cause the larger diameter threads to engage the partial threads on the inner wall of the syringe. By establishing the thread pitch as desired, the distance of travel of the plunger for each rotation of the plunger through the threaded portions can be precisely controlled, resulting in delivery of a pre-determined amount of the substances for each incremental rotation (or step-wise movement) of the plunger.

Syringe with Multiple Compartments for Storage of Components of Medicament

Turning to FIGS. 9-13, a reconstitution syringe 210 of the present invention permits individual components of a multi-component medicament or other preparation to be stored in separate compartments within the lower chamber of the syringe. The components of the multi-component preparation may be mixed within the syringe when desired for use. Many of the components of the reconstitution syringe 210 are the same as those in the syringes 10 and 110 described above, and therefore like reference numerals preceded by the numeral "2", or preceded by the "2" instead of the numeral "1", are used to indicate like elements.

Figure 9:
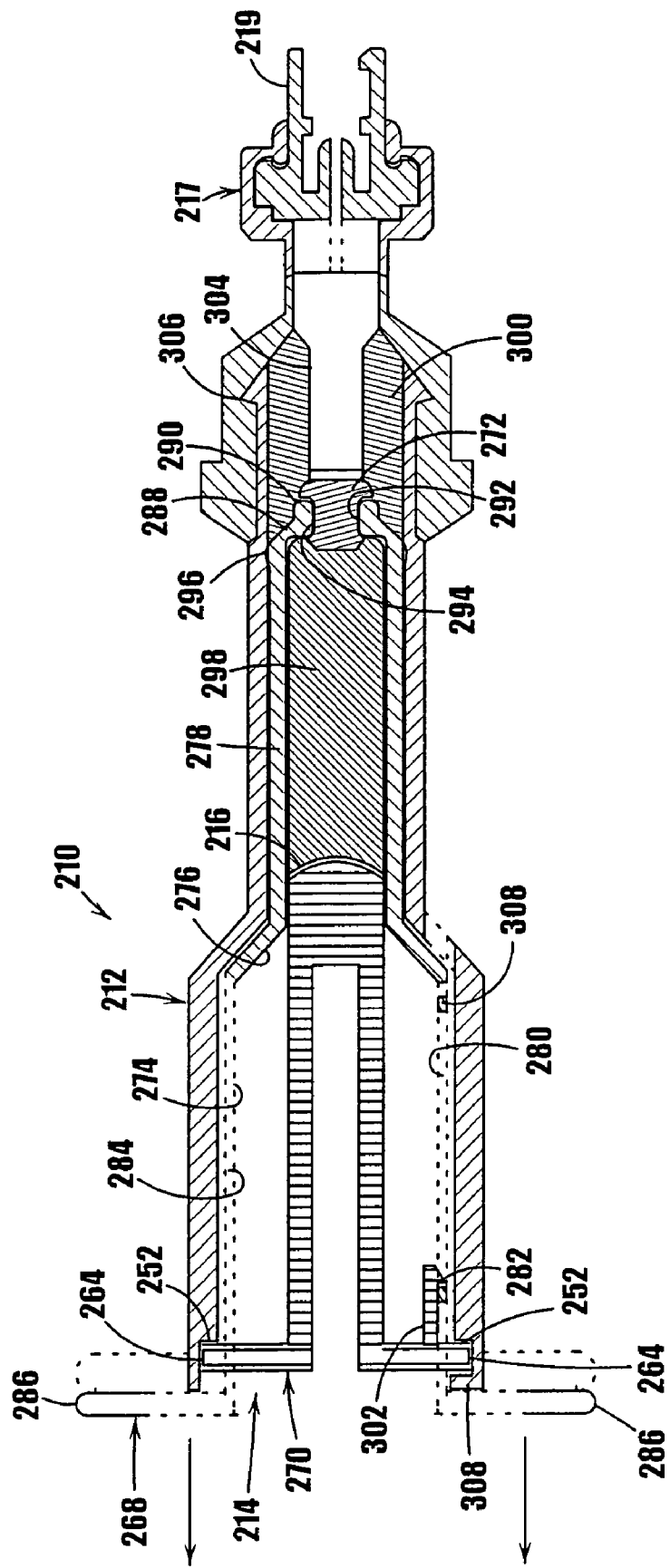
FIG. 9 is a somewhat schematic, cross-sectional view of a reconstitution syringe embodying the present invention.
Figure 10:
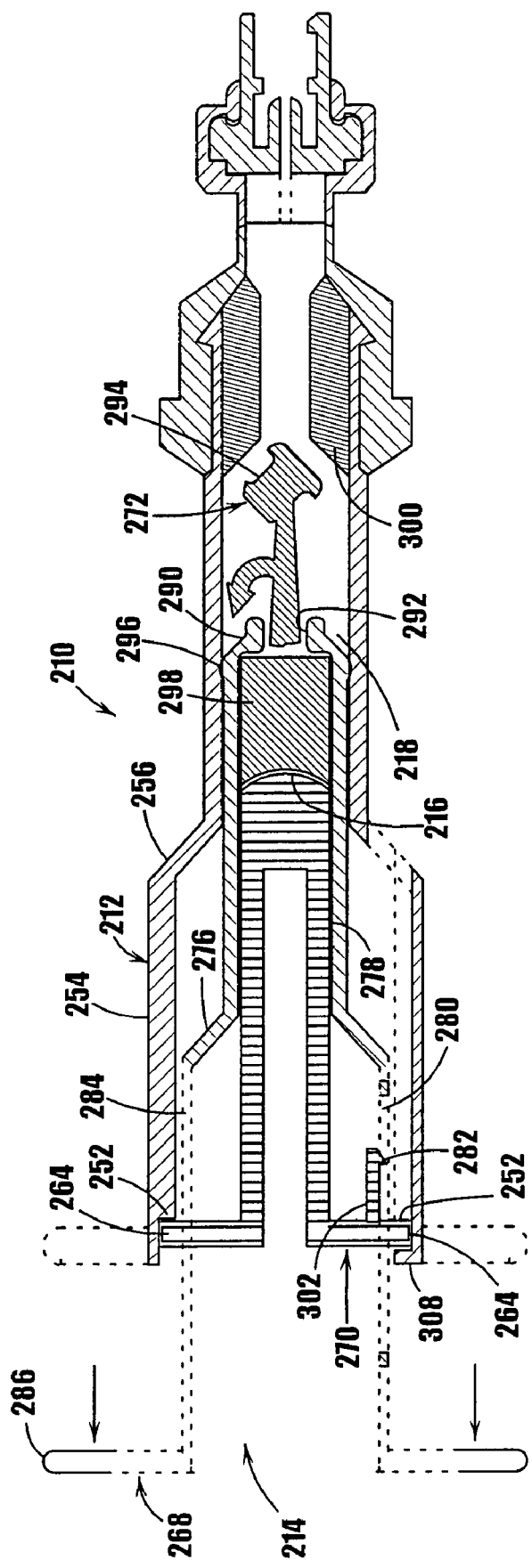
FIGS. 10 through 13 are somewhat schematic, cross-sectional views of the reconstitution syringe of FIG. 9 illustrating progressively the movement of the outer frame of the plunger relative to the closure member to intermix the multi-component preparation, the mixing of the preparation, and the dispensing of the mixed preparation.

As shown in FIG. 10, in this embodiment of the invention, the syringe body 212 defines an upper chamber 254, a transition portion 256 and a lower chamber 218. As shown in FIG. 9, the inside wall of the upper chamber 254 defines two sets of steps 252 formed on opposite sides of the inner wall of the upper chamber relative to each other. Each set of steps 252 defines an approximately helical path. One set of steps 252 is oriented to allow travel along the steps in the direction from the top of the upper chamber 254 toward the lower chamber 218 of the syringe body. The second set of steps 252 is oriented in the opposite direction to prevent movement of the plunger in that direction.

Referring to FIG. 9, the plunger 214 comprises an outer frame 268, a closure member 270, and an elastomeric plug 272. The outer frame 268 of the plunger fits slidingly within the outer body 212 of the syringe. Preferably, the outer frame 268 defines an upper portion 274, a transition portion 276, and a lower portion 278, with each section having a diameter slightly less than the diameter of the corresponding portion of the body 112 of the syringe. As shown in FIG. 9, in the storage mode, the outer frame 268 of the plunger extends from the top of the syringe body 212 to a point within the lower chamber 218 of the syringe body. The extent to which the outer frame 268 of the plunger assembly extends within the inner chambers of the syringe body can be varied depending upon the relative amounts of the components to be contained within the syringe during storage.

As shown typically in FIG. 9, on the inside wall of the upper portion 274 of the outer frame 268, an axial slot 280 is provided which, as described below, corresponds in position to a snap engagement 282 and one of the two cam-like members 264 on the closure member 270 of the plunger. A second axial slot 284 is provided in the inside wall of the upper portion 274 of the outer frame 268 for receiving a second cam-like member 264 formed on the closure member 270. As described below, the axial slots 280, 284 allow the outer frame 268 to be withdrawn from the syringe during use with the closure member 270 held stationary. A flange 286 is provided at the top of the outer frame 268 for the user to grip the outer frame in use.

The distal end 288 of the lower portion 278 of the outer frame 268 defines a generally frustoconical portion 290 defining therein a central opening 292. During storage, an elastomeric plug 272 is secured within the opening 292 to seal the end of the outer frame. The distal end 288 of the outer frame is shaped to fit into a complementary shaped annular groove 294 formed on the elastomeric plug 272 to hold the elastomeric plug in place and form a seal between the distal end of the outer frame and the plug. The elastomeric plug 272 may be made of any appropriate material known to those skilled in the art for use in storage of medicaments or other substances to be contained within the syringe, such as, for example, vulcanized rubber or any of numerous different types of polymeric materials.

An annular protuberance 296 is provided on the outer frame 268 at the base of the frustoconical portion 290. The annular protuberance 296 fits frictionally within the lower chamber 218 of the syringe body 212 to form a seal between the outer frame of the plunger and the syringe body. As can be seen in FIG. 9, the frustoconical portion 290 of the distal end 288, the elastomeric plug 272, and the annular protuberance 296 define a boundary within the lower chamber of the syringe body and divide the lower chamber of the syringe body into two compartments 298 and 300.

The closure member 270 is slidingly received within the outer frame 268 of the plunger. As can be seen, the closure member is generally cylindrical, and extends from the top of the upper chamber 254 of the syringe body to a pre-determined location within the lower portion of the outer frame 268. The predetermined point is at a point corresponding to the top of the lower chamber 218 of the syringe body. At the end of the closure member 270 within the lower chamber 218 of the syringe is a resealable stopper 216, which hermetically seals the top of the first compartment 298 of the syringe. In this embodiment of the invention, the resealable stopper 216 forms a hermetic seal with the inner surface of the outer frame 268 of the plunger assembly 214.

At the end of the closure member 268 opposite the fusible stopper 216, the closure member defines two opposed cam-like members 264 that extend perpendicularly from the axial wall of the closure member. The cam-like members 264 cooperate with the steps 252 formed on the inner wall of the upper chamber 254 of the syringe body to provide step-wise movement of the plunger assembly during dispensing of the multi-component medicament or other preparation. In the illustrated storage mode of the reconstitution syringe, one cam-like member 264 is engaged with the uppermost step 252 formed on the inner wall of the syringe body. On at least one of the cam-like members, an arm 302 extends perpendicularly from the cam-like member within the inner wall of the outer frame 268 of the plunger. At the end of the arm 302, a snap engagement 282 is provided. The snap engagement 282 fits within the corresponding axial slot 280 on the outer frame.

As shown in FIG. 9, in the storage mode, the syringe body 212, the outer frame 268 of the plunger, the elastomeric plug 272 and the closure member 270 define two compartments 298, 300 which are used to contain the two components of the medicament or other multi-component preparation. The first compartment 298 is located within the outer frame 268 of the plunger and is bounded by the fusible stopper 216 of the closure member 270 of the plunger, the frustoconical portion 288 of the outer frame of the plunger, and the elastomeric plug 272. The first compartment 298 is used to contain a first component of a medicament or other multi-component preparation, such as, for example, a saline solution or a solvent. The first compartment 298 may be filled by inserting a needle or other injection device through the fusible stopper 216 as described above and filling the first compartment with the first component of the preparation. After the filling step is complete, the resealable member of the fusible stopper is heated to seal the needle puncture and prevent ingress of air. As described above, the resealable member may be heated using a laser as described above.

The second compartment 300 is located within the lower chamber 218 of the syringe body 212 and is bounded by the frustoconical portion 288 of the outer frame of the plunger, the elastomeric plug 272 and the dispensing tip 217 described in further detail below. The second compartment 300 is used to contain a second component of the medicament or other multi-component preparation, such as, for example, a lyophilized product, a powder or a second fluid.

At the dispensing end 217 of the syringe, a dispensing mechanism is provided. In the embodiment of the invention illustrated in FIG. 9, the dispensing mechanism comprises a central post 304 defining therein at least one channel that communicates with the second compartment 300 inside the lower chamber 218 of the syringe. At the end of the syringe body 212, the syringe body defines an annular retention shoulder 306. Any appropriate dispensing tip mechanism known to one skilled in the art can be fixedly attached to the syringe body. For example, the conventional connection device marketed under the trade name LUER-LOK can be used at the dispensing tip of the syringe to allow attachment of disposable needles. In this embodiment of the invention, as the closure member 270 of the plunger assembly advances into the syringe, the medicament is dispensed through a channel in the post 304 and through the disposable needle (not shown). Other needle connection means, such as threaded fittings, elastomeric plugs, or fitted end caps equally may be used to attach a needle to the end of the syringe. The lower end of the syringe body may be shaped or threaded as required to accommodate the selected needle connection means. A cap or other means (not shown) to hermetically seal the dispensing end of the syringe may be used until the hypodermic or other needle is connected to the syringe to dispense the medicament or other substance therein.

In use, the reconstitution syringe operates in the following manner. As indicated by the arrows in FIG. 10, the outer frame 268 of the plunger 214 is withdrawn from the syringe body 212. As the outer frame 268 is initially withdrawn, the closure member 270 is held stationary by a retention shoulder 308 formed on the top of the syringe body 212 that interacts with the cam-like member 264 to prevent outward axial movement of the closure member. The axial slots 280, 284 in the upper portion of the outer frame 268 allow the outer frame to be withdrawn past the cam-like members 264 and the snap engagement 282.

As the outer frame 268 is withdrawn, the volume of the first compartment 298 is reduced, causing the fluid pressure in the first compartment 298 to increase. When the pressure in the first compartment 298 is sufficiently high, the elastomeric plug 272 is released from the frustoconical portion 290 formed on the distal end 288 of the outer frame. The release of the elastomeric plug 272 results in a fluid communication path being formed between the first compartment 298 and the second compartment 300, allowing the component in the first compartment to flow through the central opening 294 and mix with the component in the second compartment 300.

Figure 11:
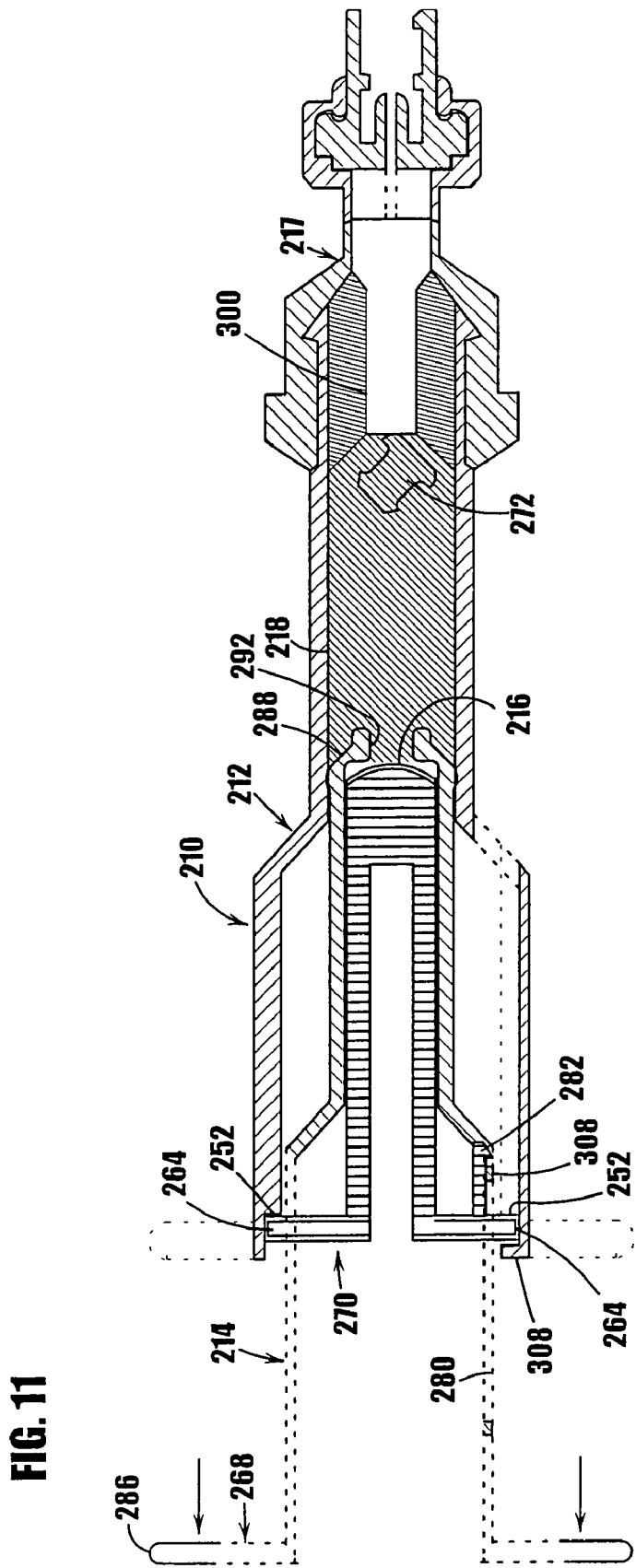

As shown in FIG. 11, the outer frame 268 of the plunger is withdrawn from the syringe until the snap engagement 282 engages a corresponding engagement portion 308 formed at the base of the axial slot 280 in the outer frame 268. When the outer frame 268 is fully withdrawn, the fusible stopper 272 of the closure member 270 is typically positioned adjacent to the opening 292. As shown in FIG. 11, when the outer frame 268 is fully withdrawn, a single compartment is formed for the medicament or other multi-component substance, bounded by the inner walls of the lower chamber 218 of the syringe body, the fusible stopper 216 of the plunger, the distal end 288 of the outer frame, and the dispensing end 217 of the syringe.

After the outer frame 268 has been fully withdrawn, the syringe may be shaken to mix the two components of the medicament or other preparation within the chamber 218.

The elastomeric plug 272 acts like a mixing ball and provides a mechanism to obtain complete mixing of the components. This provides the advantage of assuring that the medicament or other multi-component preparation contained in the syringe after mixing provides the desired dose of the medicament for each predetermined movement of the plunger.

Figure 12:
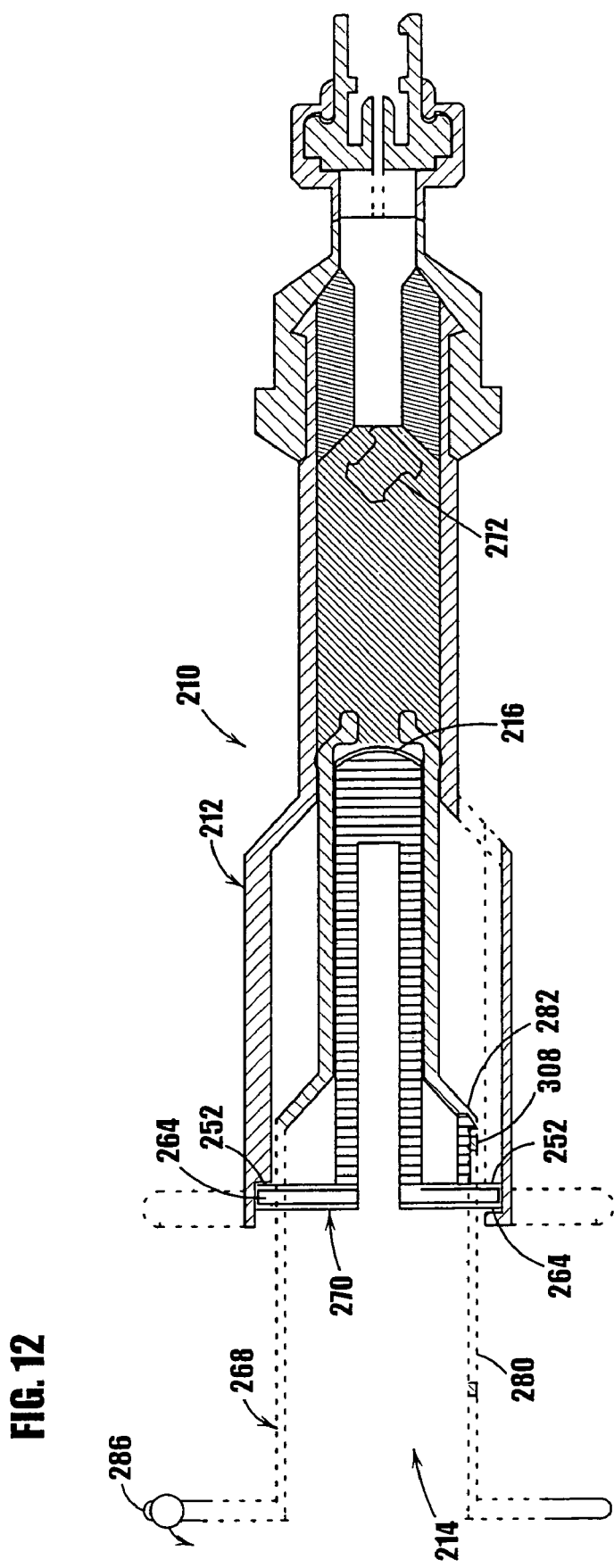
Figure 13:
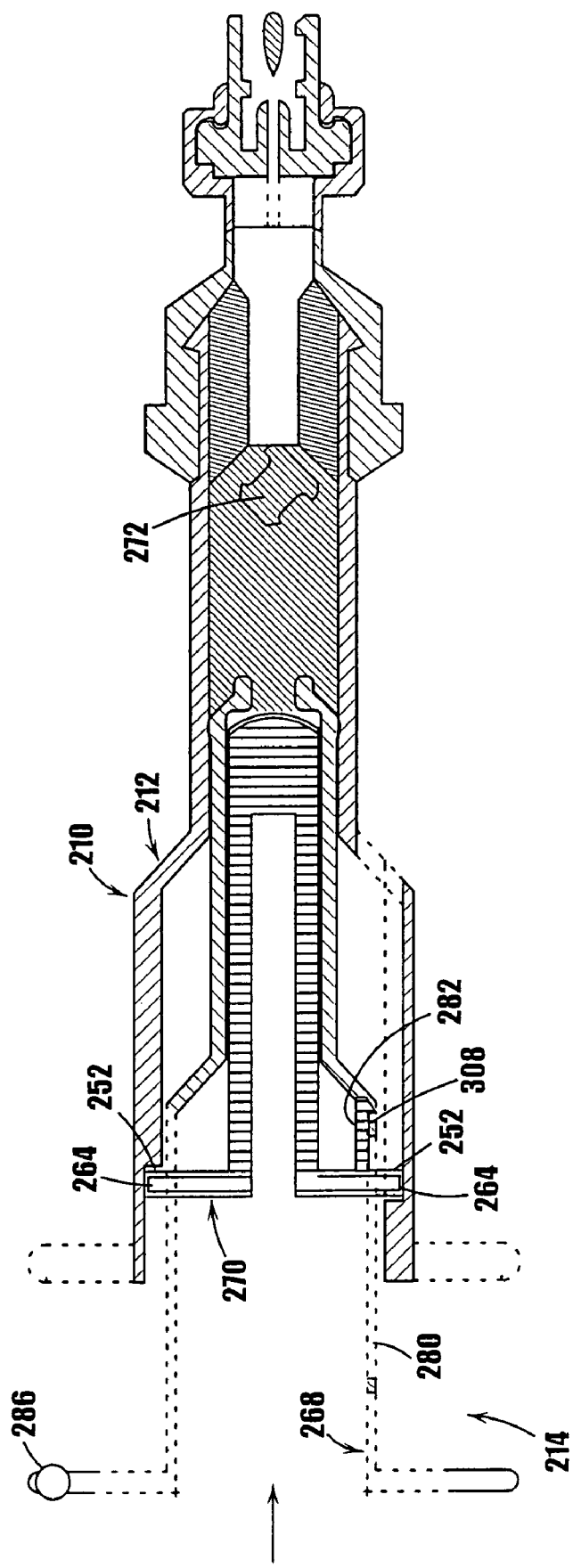

The snap engagement 282 and the engagement portion 308 act together to capture the closure member 270 in the outer frame 268 and thereby fixedly secure the two parts together. The cam-like members 264 are maintained within the axial slots 280, 284 in the side of the outer frame 268. As a result, the outer frame 268 and closure member 270 move together and act as a plunger assembly to dispense the mixed medicament from the syringe. As shown in FIGS. 12 and 13, as the outer frame 268 is rotated in the direction that causes the plunger mechanism to travel in the direction toward the dispensing tip of the syringe (typically clockwise), the cam-like members 264 on the closure member 270 cooperate with the steps 252 on the inner wall of the upper chamber of the syringe to provide step-wise movement of the upper frame and closure member into the syringe. As described above, as the closure member travels one step into the syringe, the base of the closure member travels a precise distance, and a precise volume of the medicament or other multi-component substance contained therein can be delivered.

In another embodiment of the invention, the inner walls of the upper chamber of the syringe body are smooth, and the cam-like members on the closure member fit within the upper chamber of the syringe. This allows the entire contents of the syringe to be delivered in a single dose without step-wise movement of the plunger mechanism.

As described above, those skilled in the pertinent art may recognize based on the teachings herein that the structure for performing the function of controlling the travel of the plunger can take any of numerous different configurations that are currently or later become known for performing this function, such as any of the structures disclosed in the above-mentioned co-pending patent application.

The preferred embodiments disclosed herein are to be considered exemplary of the principles of the present invention and are not intended to limit the invention to the embodiments described. In addition, various modifications will be apparent to those skilled in the pertinent art based on the teachings herein without departing from the spirit or scope of the invention disclosed herein and defined in the claims. Accordingly, this detailed description of the preferred embodiments is to be taken in an illustrative, as opposed to a limiting sense.

What is claimed is:

1. A method comprising the following steps:
   providing a syringe including a syringe body, a plunger slidably received within the syringe body, and a resealable stopper including a resealable portion fusible in response to the application of thermal energy thereto;
   sterilizing an exposed surface of the stopper;
   penetrating the stopper with a needle coupled in fluid communication with a source of a substance;
   introducing the substance through the needle and into the interior of the syringe body;
   withdrawing the needle from the stopper; and
   applying sufficient thermal energy to the penetrated region of the resealable portion of the stopper to fuse the penetrated region and form a substantially gas-tight seal between the penetrated region and the interior of the syringe body.

2. A method as defined in claim 1, wherein the introducing step includes introducing any of the following substances through the needle and into the interior of the syringe body: a vaccine, a medicament, a pharmaceutical preparation, a cosmetic and a food product.

3. A method as defined in claim 1, further comprising sterilizing at least the interior of the syringe body, introducing a sterile substance through the needle and into the interior of the syringe body, and maintaining the interior of the syringe body and substance sterile during filling and storage thereafter.

4. A method as defined in claim 1, wherein the applying step includes applying laser radiation to the penetrated region of the resealable portion to fuse the penetrated region and form a substantially gas-tight seal between the penetrated region and the interior of the syringe body.

5. A method as defined in claim 4, wherein the applying step further includes applying with a laser sufficient energy to the resealable portion to fuse the resealable portion while preventing heating of the substance within the interior of the syringe body.

6. A method as defined in claim 5, further comprising applying laser energy at a power of less than about 10 watts.

7. A method as defined in claim 1, further comprising the step of venting air or other gas out of the interior of the syringe body during the step of introducing the substance through the needle and into the interior of the syringe body.

8. A method as defined in claim 1, further comprising hermetically sealing the interior of the syringe body and preventing contamination of the interior of the syringe body during filling and storage of the syringe.

9. A method comprising the following steps:
   providing a device including a sealed, empty storage chamber, and including a penetrable and thermally resealable portion in fluid communication with the storage chamber including a body defining a predetermined wall thickness that substantially absorbs laser radiation at a predetermined wavelength and power and substantially prevents the passage of such radiation therethrough, and a penetrable region that is penetrable with a filling member and that defines a predetermined color and opacity that substantially absorbs the laser radiation at the predetermined wavelength and power to hermetically seal an aperture therein;
   sterilizing an exposed surface of the penetrable and thermally resealable portion;
   penetrating the penetrable and thermally resealable portion with a filling member coupled in fluid communication with a source of a sterile food product;
   introducing the sterile food product through the filling member and into the storage chamber;
   withdrawing the filling member from the penetrable and thermally resealable portion;
   applying laser radiation from a laser source at the predetermined wavelength and power to an aperture formed in the penetrable region of the body;
   substantially absorbing within the penetrable region of the body the laser radiation at the predetermined wavelength and power and substantially preventing the passage of radiation through the predetermined wall thickness of the body; and
   hermetically sealing the aperture in the penetrable region of the body with the laser radiation within a predetermined time period and, in turn, hermetically sealing the sterile food product within the chamber of the device.

10. A method as defined in claim 9, further comprising sterilizing the sealed empty device prior to introducing the sterile food product therein.

11. A method as defined in claim 9, further comprising sterilizing at least the sealed, empty storage chamber, and the penetrable and thermally resealable portion in fluid communication with the storage chamber, introducing the sterile food product through the filling member and into the storage chamber, and maintaining the storage chamber and food product sterile during filling and storage thereafter.

12. A method as defined in claim 9, wherein the applying step further includes applying with a laser sufficient energy to the resealable portion to hermetically seal the resealable portion while preventing heating of the food product within the storage chamber.

13. A method as defined in claim 12, wherein the applying step further includes applying laser energy at a power of less than about 10 watts.

14. A method as defined in claim 9, further comprising the step of venting air or other gas out of the storage chamber during the introducing step.

15. A method as defined in claim 9, further comprising hermetically sealing the storage chamber and preventing contamination of the storage chamber during filling and storage of the device.

16. A method as defined in claim 1, wherein the device is a syringe.

17. A method as defined in claim 1, further comprising the step of using the body to thermally insulate the sterile food product in the chamber from the laser energy applied by the laser source to avoid thermal damage to the sterile food product in the chamber.

18. A method as defined in claim 1, further comprising the step of introducing the sterile food product through a first fluid passageway of the filling member, and allowing fluid to flow out of the chamber of the device through a second fluid passageway upon introducing the sterile food product from the first fluid passageway into the chamber.

19. A method as defined in claim 1, wherein the filling member is a needle.

20. A method comprising the following steps:
providing a device including a first body portion defining a first compartment forming a first sealed, empty storage chamber; a second body portion defining a second compartment forming a second sealed storage chamber; and a penetrable and thermally resealable portion in fluid communication with at least the first storage chamber, wherein the first and second compartments define a storage state in which the first and second compartments are hermetically sealed relative to each other, and a dispensing state in which the first and second compartments are in fluid communication with each other;
sterilizing an exposed surface of the penetrable and thermally resealable portion;
penetrating the penetrable and thermally resealable portion with a filling member coupled in fluid communication with a source of a first product component of a sterile food product;
introducing the first product component through the filling member and into the first sealed, empty storage chamber;
withdrawing the filling member from the penetrable and thermally resealable portion; and
applying sufficient thermal energy to the penetrated region of the penetrable and thermally resealable portion to fuse the penetrated region and form a substantially gas-tight seal between the penetrated region and the first compartment.

21. A method as defined in 20, further comprising:
filling the storage chamber of the second compartment with a second product component and sealing the second product component within the second compartment; and
maintaining the filled first and second compartments in the storage state hermetically sealed relative to each other while in the storage state.

22. A method as defined in claim 21, further comprising moving at least one of the first and second compartments from (i) the storage state in which the first and second product components are hermetically sealed relative to each other and are prevented from intermixing, to (ii) the dispensing state in which the first and second compartments are in fluid communication with each other, and further comprising intermixing the first and second product components into a food product, and dispensing the food product.

* * * * *

UNITED STATES PATENT AND TRADEMARK OFFICE
CERTIFICATE OF CORRECTION

PATENT NO. : 7,779,609 B2
APPLICATION NO. : 11/714004
DATED : August 24, 2010
INVENTOR(S) : Daniel Py It is certified that error appears in the above-identified patent and that said Letters Patent is hereby corrected as shown below:

In The Claims:

Column 17, line 23, claim 16, "as defined in claim 1" should be changed to --as defined in claim 9--

Column 17, line 25, claim 17, "as defined in claim 1" should be changed to --as defined in claim 9--

Column 17, line 30, claim 18, "as defined in claim 1" should be changed to --as defined in claim 9--

Column 17, line 36, claim 19, "as defined in claim 1" should be changed to --as defined in claim 9--

Signed and Sealed this

Second Day of November, 2010

David J. Kappos
*Director of the United States Patent and Trademark Office*